(12) United States Patent
Weiman et al.

(10) Patent No.: US 8,864,798 B2
(45) Date of Patent: Oct. 21, 2014

(54) TRANSVERSE CONNECTOR

(75) Inventors: Mark Weiman, Coatesville, PA (US); Ryan Watt, Boyertown, PA (US)

(73) Assignee: Globus Medical, Inc., Audubon, PA (US)

( * ) Notice: Subject to any disclaimer, the term of this patent is extended or adjusted under 35 U.S.C. 154(b) by 1486 days.

(21) Appl. No.: 12/016,495

(22) Filed: Jan. 18, 2008

(65) Prior Publication Data
US 2009/0187217 A1   Jul. 23, 2009

(51) Int. Cl.
*A61B 17/70* (2006.01)

(52) U.S. Cl.
CPC .................... *A61B 17/7052* (2013.01)
USPC ............ 606/253; 606/250; 606/251; 606/252

(58) Field of Classification Search
USPC .................................................. 606/250–253
See application file for complete search history.

(56) References Cited

U.S. PATENT DOCUMENTS

| | | |
|---|---|---|
| 5,010,879 A | 4/1991 | Moriya et al. |
| 5,380,325 A | 1/1995 | Lahille |
| 5,676,665 A * | 10/1997 | Bryan ........................... 606/252 |
| 6,090,111 A | 7/2000 | Nichols |
| 6,565,565 B1 | 5/2003 | Yuan et al. |
| 6,669,729 B2 | 12/2003 | Chin |
| 6,740,086 B2 | 5/2004 | Richelsoph |
| 6,755,829 B1 | 6/2004 | Bono et al. |
| 6,786,903 B2 | 9/2004 | Lin |
| 7,081,117 B2 | 7/2006 | Bono et al. |
| 7,125,426 B2 | 10/2006 | Moumene et al. |
| 7,261,714 B2 | 8/2007 | Richelsoph |
| 7,282,064 B2 | 10/2007 | Chin |
| 2002/0120272 A1 | 8/2002 | Yuan et al. |
| 2005/0080416 A1 | 4/2005 | Ryan et al. |
| 2005/0119657 A1 | 6/2005 | Goldsmith |
| 2005/0228326 A1 | 10/2005 | Kalfas et al. |
| 2006/0009766 A1 * | 1/2006 | Lee et al. ........................ 606/61 |
| 2006/0200128 A1 | 9/2006 | Mueller |
| 2007/0299446 A1 | 12/2007 | Chin |
| 2008/0045955 A1 | 2/2008 | Berrevoets et al. |

* cited by examiner

*Primary Examiner* — Eduardo C Robert
*Assistant Examiner* — Julianna N Harvey (57) ABSTRACT

A transverse connector system having a first and a second locking head, and a transverse rod that is secured by the first and second locking heads. The first and second locking heads are provided with a first and second pivot arm for engaging and securing first and second elongated rods. The first and second locking heads each simultaneously engage and secure the transverse and elongated rods separately.

7 Claims, 11 Drawing Sheets

TRANSVERSE CONNECTOR

FIELD OF THE INVENTION

The present invention is generally directed for use in stabilizing the spine. In particular, the present invention is directed to a device that provides additional support for a posterior rod construct.

BACKGROUND OF THE INVENTION

In the United States, millions are affected by back pain. Most patients respond well to non-surgical treatments. However, many others are required to find other solutions to alleviate the pain. If the back pain persists and in addition, other symptoms such as arm pain and neurological dysfunction occur, the cause may be related to any number of problems associated with the vertebral column. Surgery is an option for those that require stabilization of the spine. To alleviate the symptoms and overcome the problems, a surgeon may utilize various devices to correct the structural integrity of the vertebrae. For instance a surgeon may align the vertebrae using a posterior rod construct. In this type of system, a surgeon places anchoring devices such as screws and/or hooks that are capable of receiving elongated rods on either side of the vertebrae covering at least one level in length. Since each rod is fixed to the vertebrae, the rod construct provides structural integrity. Thus, when a posterior dual rod construct is used to stabilize the human spine, it is often necessary to connect the elongated rods to further increase the stability of the overall construct. To connect the elongated rods to provide additional stability, surgeons typically use a horizontal transverse connector. In the prior art, transverse connectors generally utilize a mechanism wherein the elongated rods and the transverse rods are fastened separately. These types of systems also generally sacrifice adjustability or stability.

For instance, in one type of system, a set screw is used to lock the transverse connector to the elongated rod and then another set screw is used to lock the position of the transverse rod. In other words, the elongated rod is fastened and then the transverse rod fastened. In this type of system, simplicity is sacrificed since two separate locking mechanisms are utilized.

In another type of transverse connection, a hook system is used. This type of system generally fastens the transverse connector to the elongated rods using a hook type arm, however this type of system does not provide a means for allowing the transverse rod to be moved laterally and positioned in any angle along the horizontal axis. In other words, the transverse rod must be the exact size required prior to positioning the transverse connector. Thus, there is a need for a transverse connector that provides a locking mechanism that is capable of locking the transverse connector to the elongated rods and the transverse rod without sacrificing either adjustability or the stability of the posterior rod construct. There is also a need for a T-connector that provides surgeons with a locking mechanism that is easy to use and which requires very little time to execute in locking both the elongated and transverse rods.

SUMMARY OF THE INVENTION

According to one aspect of the invention, a transverse connector system is provided. The system includes a first and a second locking head and a transverse rod having opposing first and a second ends, the first end being retained within a portion of the first locking head and the second end being retained within a portion of the second locking head. The first locking head includes a first pivot arm for engaging and capturing the first elongated rod and the second locking head having a second pivot arm for engaging and capturing the second elongated rod. The first locking head is provided with a first locking mechanism which simultaneously secures the first end of the transverse rod and the first elongated rod. The second locking head also includes a second locking mechanism for simultaneously securing the second end of the transverse rod and the second elongated rod.

According to another aspect of the transverse connector system, the transverse connector includes a first pivot arm that is coupled to the first locking head by at least two lateral elements extending from a first base element of the first locking head and the second pivot arm is coupled to the second locking head by at least two lateral elements extending from a second base element of the second locking head.

According to another aspect of the invention, there is a method for stabilizing a posterior rod construct position in a spine comprising the steps of positioning a plurality of bone anchors on the spine and positioning at least two elongated rods so that the bone anchors capture and retain the at least two elongated rods. The method also includes positioning a transverse connector to be coupled to the at least two elongated rods. The transverse connector includes a transverse rod with opposing first and second ends, the first end being retained within a portion of the first locking head and the second end being retained within a portion of the second locking head, and the first locking head having a first pivot arm for engaging and capturing one of the at least two elongated rods and the second locking head having a second pivot arm for engaging and capturing a second one of the at least two elongated rods. The method also includes securing the first end of the transverse rod and the first of the at least two elongated rods simultaneously with a fastener, and securing the second end of the transverse rod and the second of the at least two elongated rods simultaneously with a fastener.

In another aspect of the invention, a spine stabilization system for stabilizing a posterior rod construct is provided. The spine stabilization system includes a plurality of bone anchors and at least two elongated rods configured to be coupled to the plurality of bone anchors. The system also includes a transverse connector having a transverse rod with an opposing first and second ends, the first end being retained within a portion of the first locking head and the second end being retained within a portion of the second locking head. The first locking head has a first pivot arm for engaging and capturing one of the at least two elongated rods and the second locking head having a second pivot arm for engaging and capturing a second one of the at least two elongated rods. The first locking head simultaneously secures the first end of the transverse rod and the first of the at least two elongated rods and the second locking head simultaneously securing the second end of the transverse rod and the second of the at least two elongated rods.

BRIEF DESCRIPTION OF THE DRAWINGS

The attached drawings illustrate the elements of the present invention. Design and utility features of the present invention are also disclosed.

DETAILED DESCRIPTION OF THE INVENTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to limit the scope of the disclosure, including the claims, is limited to that embodiment.

Figure 1:
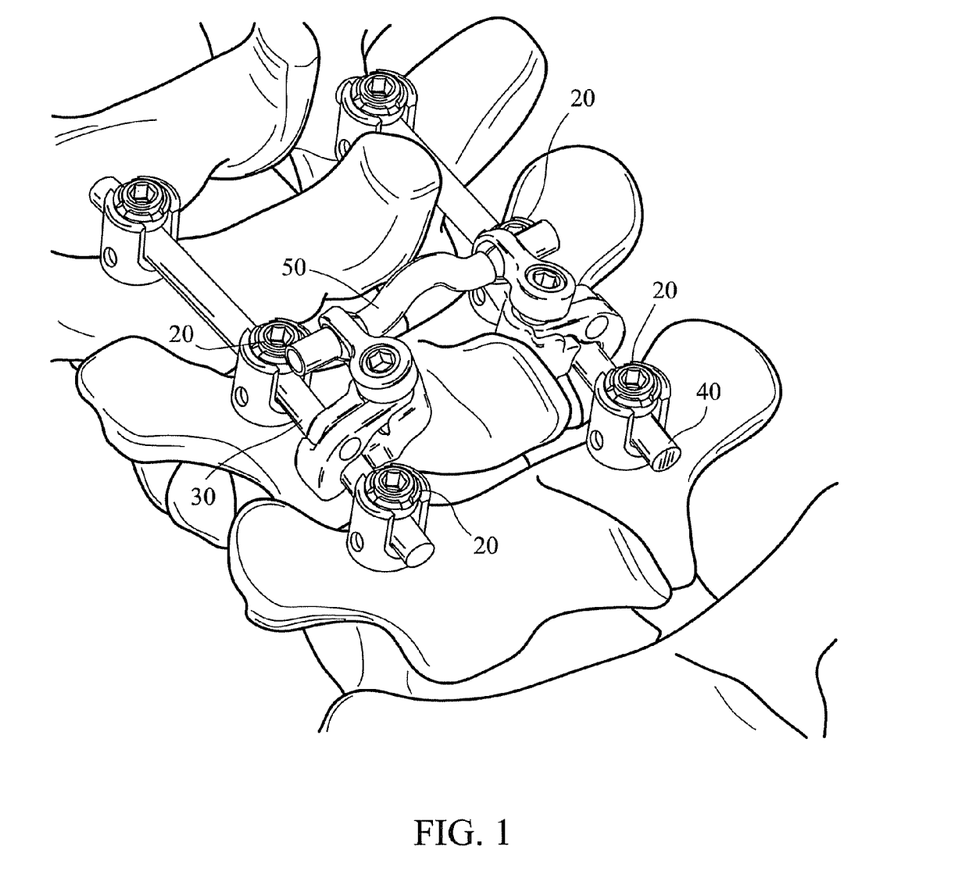
FIG. 1 is a perspective view of one embodiment of a spine stabilization system according to the invention.

Referring now to FIG. 1, one particular embodiment of a stabilization system 10 according to the invention is shown. This particular embodiment of the stabilization system 10 comprises bone anchors 20 attached to bone and elongated rods 30 and 40 which are secured to the bone anchors 20. The bone anchors 20 are attached to the bone through the use of bone screws. In addition to being secured to the bone, the bone anchors 20 are configured to engage and retain the elongated rods 30 and 40. In this particular embodiment of the invention, the elongated rods 30 and 40 can be interconnected by transverse connector 50. The transverse connector 50 provides additional stability and support for the stabilization system 10. In this particular embodiment, the transverse connector 50 is positioned between the spinous processes of the vertebrae. The transverse connector 50 is typically positioned between adjacent bone anchors, and coupled to each of the elongated rods 30 and 40, as illustrated in FIG. 1. The engaging and capturing of the transverse connector 50 to the elongated rods 30 and 40 will be discussed in greater detail with reference to FIGS. 2-9.

Figure 2:
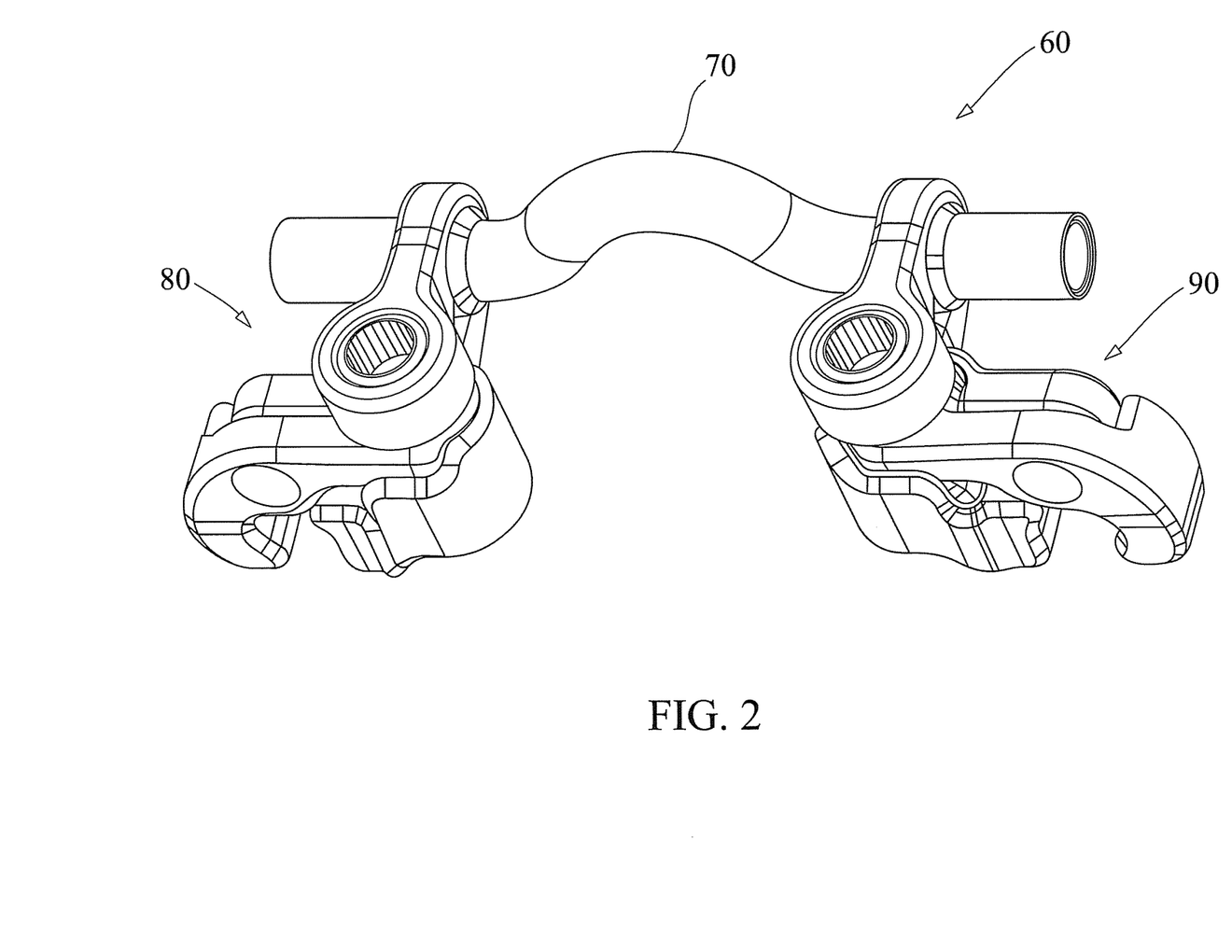
FIG. 2 is a perspective view of one particular embodiment of a transverse connector system according to the present invention.

FIG. 2 is a perspective view of one embodiment of a transverse connector 60 according to the invention. The transverse connector 60 comprises a transverse rod 70 that is captured and retained by a first locking head 80 and a second locking head 90. The first and second locking heads 80 and 90 are also configured to be coupled with elongated rods (not shown). Since each locking 80 and 90 are substantially similar, the elements and functions of a single locking head will be described for clarity and ease of understanding.

Figure 3:
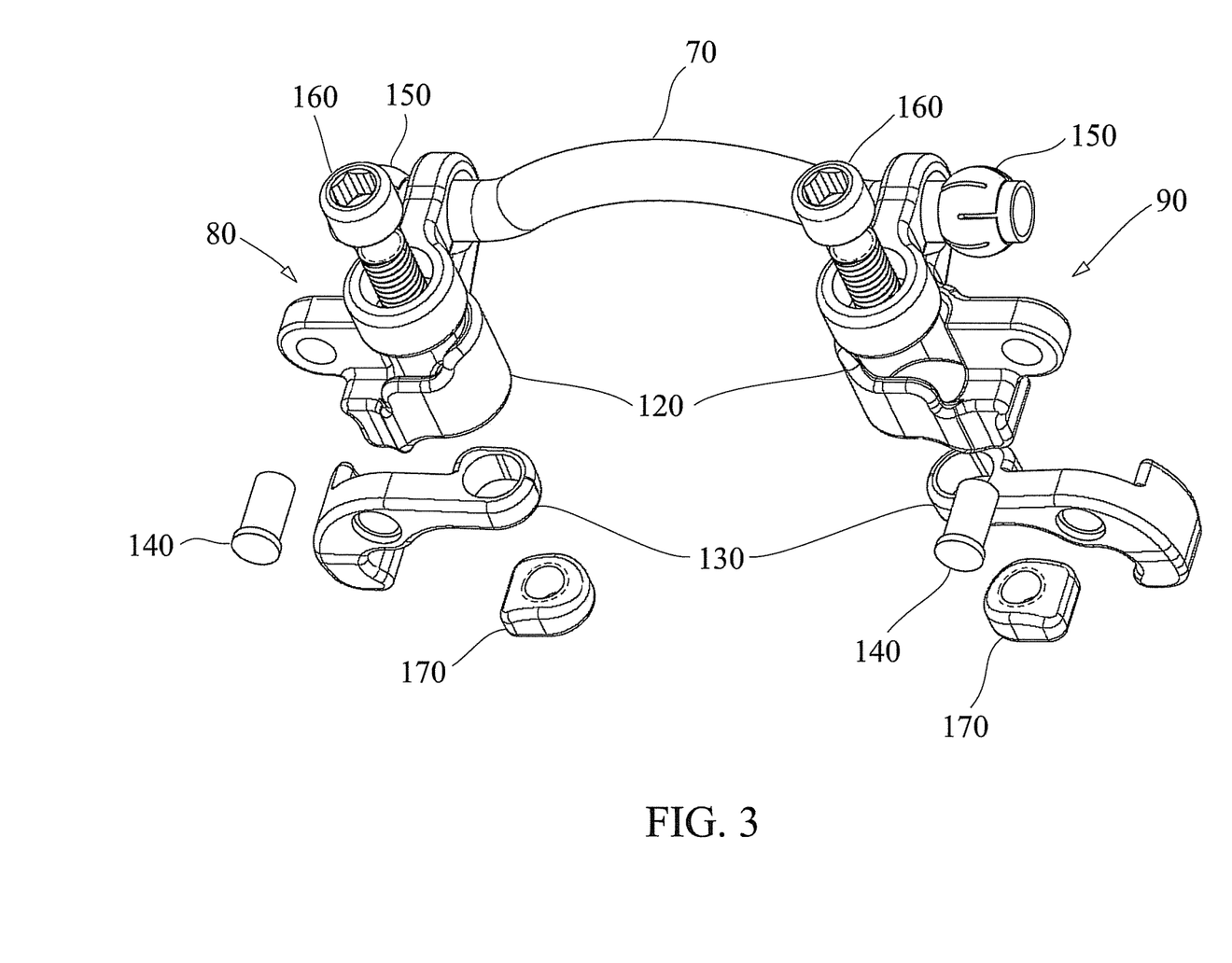
FIG. 3 illustrates the elements of the transverse connector system according to the embodiment shown in FIG. 2.

Now turning to FIG. 3, the elements comprising the first and second locking heads 80 and 90 in one particular embodiment of the invention are shown in detail. The first and second locking heads 80, 90 are each comprised of a base element 120, a pivot arm 130, a pivot pin 140, a spherical collet 150, a fastener 160, and a nut 170. As illustrated in FIG. 3, the components of the locking heads are configured and dimensioned to capture and retain the transverse rod 70 and an elongated rod by utilizing a single fastening means. Each element of the locking heads will be described in greater detail with reference to FIGS. 5-9.

Figure 4:
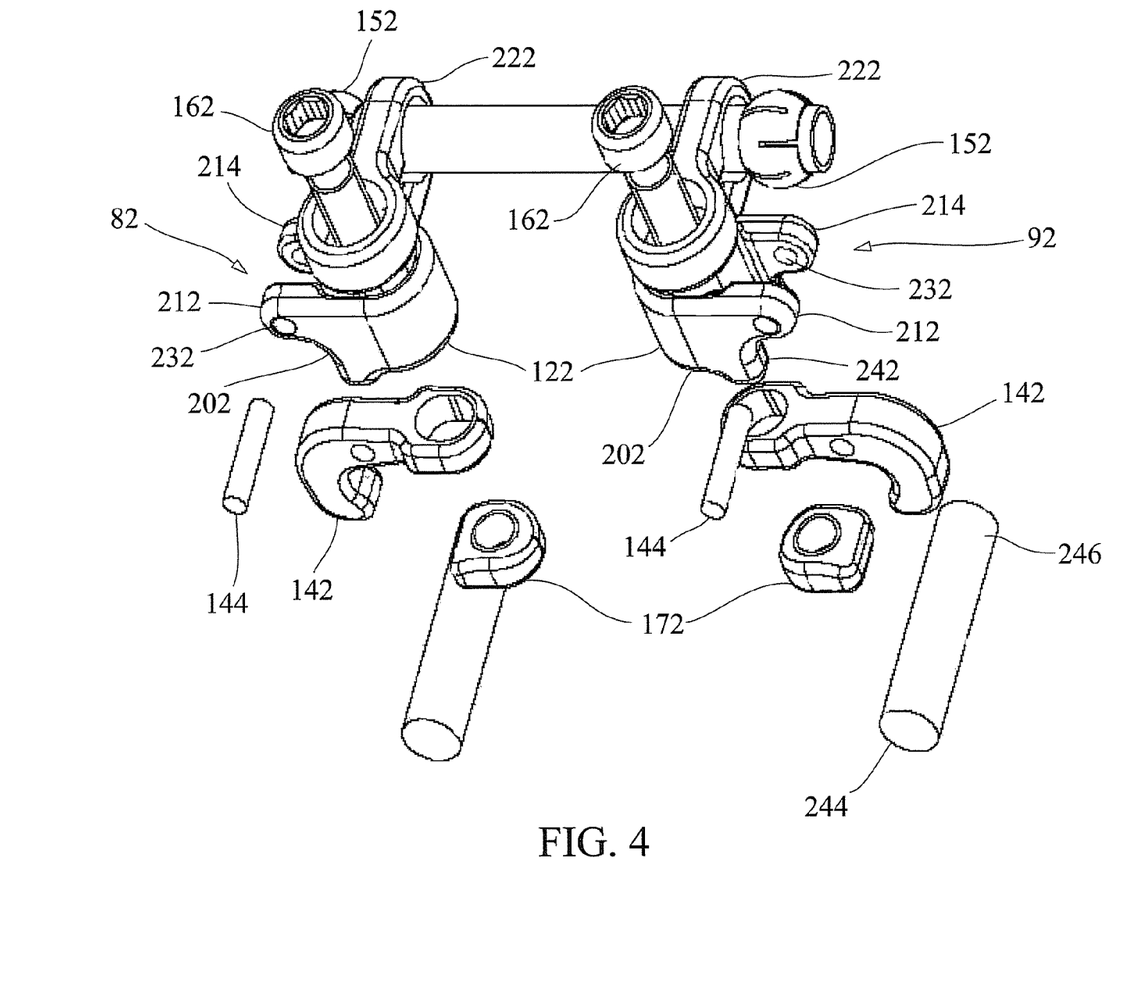
FIG. 4 is another embodiment of a transverse connector system according to the invention.

FIG. 4 is another embodiment of the present invention. In this embodiment, the first and second locking heads 82 and 92 are each comprised of a base element 122, a pivot arm 142, a pivot pin 144, a spherical collet 152, a fastener 162, and a nut 172. In this particular embodiment the elements of the locking heads 82 and 92 are similar to the preferred embodiment except that of the base element 122. In this embodiment of the invention, the base element 122 is comprised of a base portion 202, lateral elements 212, 214 and a clamping element 222. The lateral elements 212 and 214 extends laterally from the base portion 202 and are configured with a pin hole 232. The dual lateral elements 212 and 214 provide additional support and stability to the pivot arm 142. As in the preferred embodiment, the lateral end 242 is configured with a curvature for contacting and supporting a first portion 244 of an elongated rod 246. The operation of the fastening means of this embodiment are similar to the preferred embodiment, therefore the description of the simultaneous locking mechanism will be described with reference to FIGS. 5-13.

Figure 5:
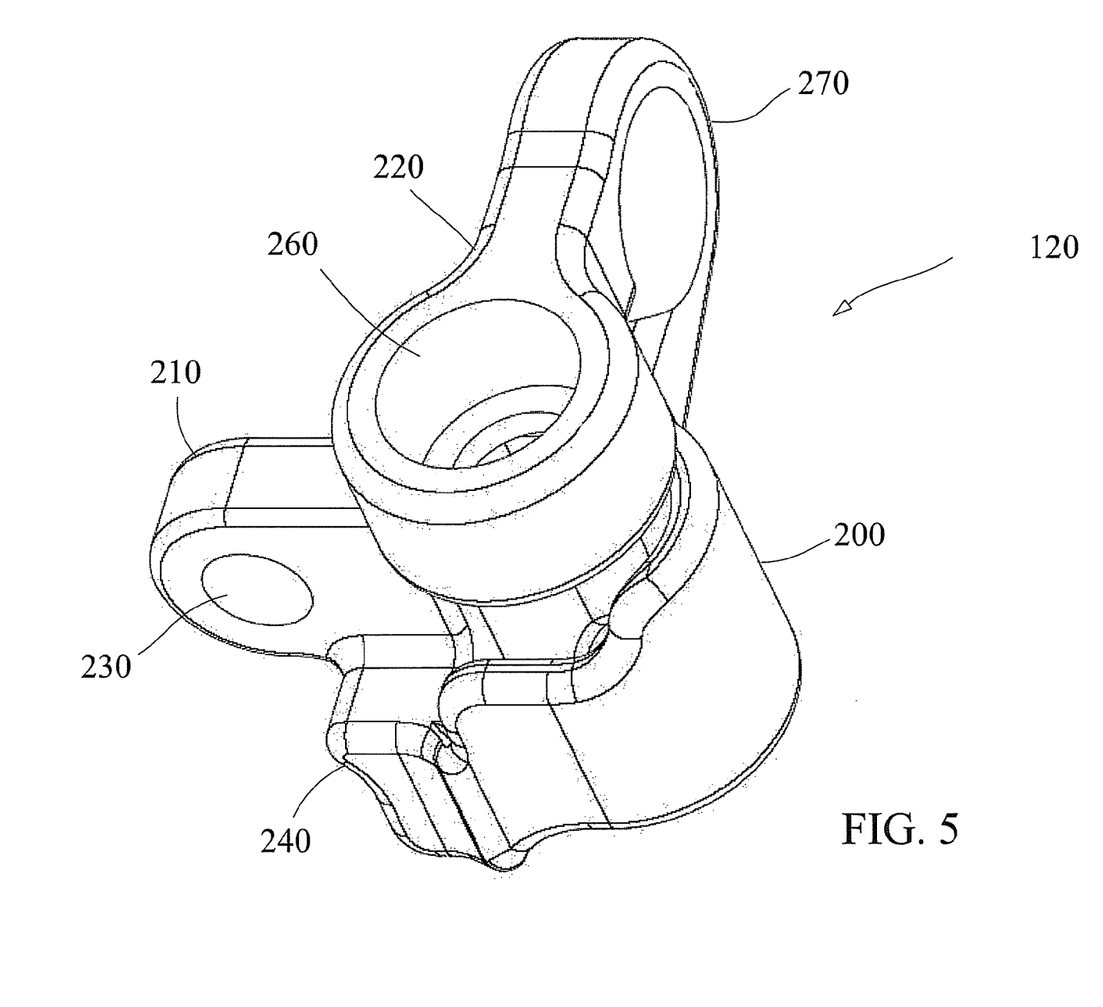
FIG. 5 illustrates the base element of a locking head component according to an embodiment of the invention.

FIG. 5 is a detailed illustration of the base element 120 as provided in the embodiment in disclosed in FIG. 3. Since the base elements 120 of locking head 80 and 90 are substantially similar, a detailed description of base element 120 of locking head 80 will be described. The base element 120 is comprised of a base portion 200, a lateral element 210 and a clamping element 220. The lateral element 210 extends laterally from the base portion 200 and is configured with a pin hole 230. The lateral end 240 of the base portion 200 extends from one vertical end of the base portion to the other vertical end of the base portion 200. The lateral end 240 is configured with a curvature for contacting and supporting a first portion of an elongated rod.

The base element 120 is also comprised of a clamping element 220, which is configured with a screw hole 260 that extends through the base portion 200 of the base element 120. The C-portion 270 of the clamping element 220 extends longitudinally from the base portion 200 to form a C-clamp and ends at the top portion of the base element 120 forming screw hole 260. The clamping element 220 is configured to retain and capture a traverse rod as illustrated in FIGS. 1-3. The base element 120 as illustrated is configured to communicate with a transverse rod and an elongated rod through the use of the lateral element 210 and the clamping element 220.

Figures 6A, 6B, 6C:
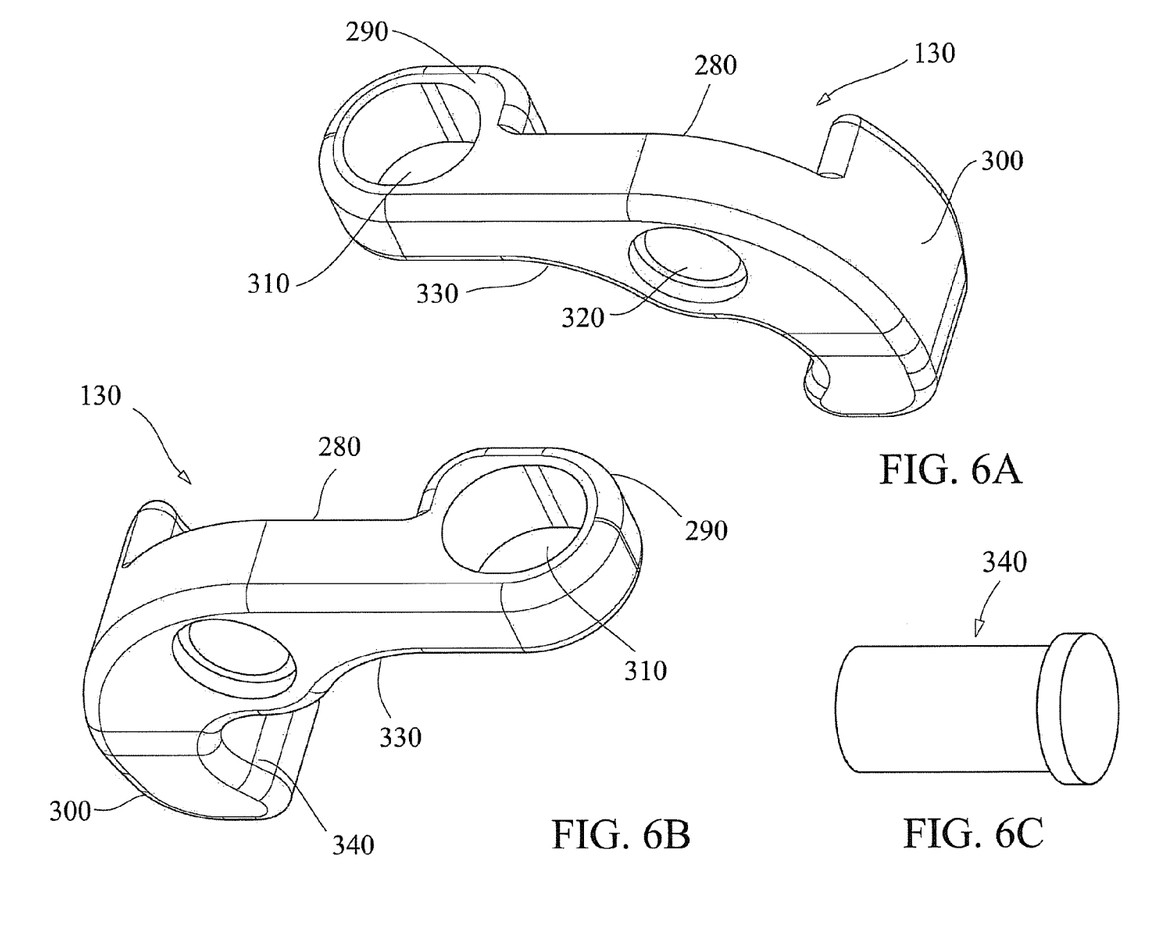
FIGS. 6A, 6B, and 6C illustrate the elements related to the pivot arm of a locking head component according to an embodiment of the invention

Now turning to FIGS. 6A-6C, the pivot arm 130 and the function as well as the structure will be described in detail. The pivot arm 130 includes a body 280, a screw hole portion 290 and a hook portion 300. The screw hole portion 290 is at an opposing end from the hook portion 300 and is configured with a screw hole 310. The body 280 of the pivot arm 130 contains a pivot arm pin hole 320 which is aligned with the pivot pin hole 230 of the lateral element 210 of the base element 120. A lower portion 330 of the body 280 of the pivot arm 130 is configured to be adapted into the base portion 200 of the base element 120 so that the pivot arm pin hole 320 and pivot pin hole 230 can be aligned easily. A pivot pin 340, as shown in FIG. 6C, is used to connect the pivot arm 130 and the base element 120 together. The hook element 300 of the pivot arm 130 is configured with a curvature 340 so that the hook element 200 is adapted to communicate with a second portion of an elongated rod.

Figure 7:
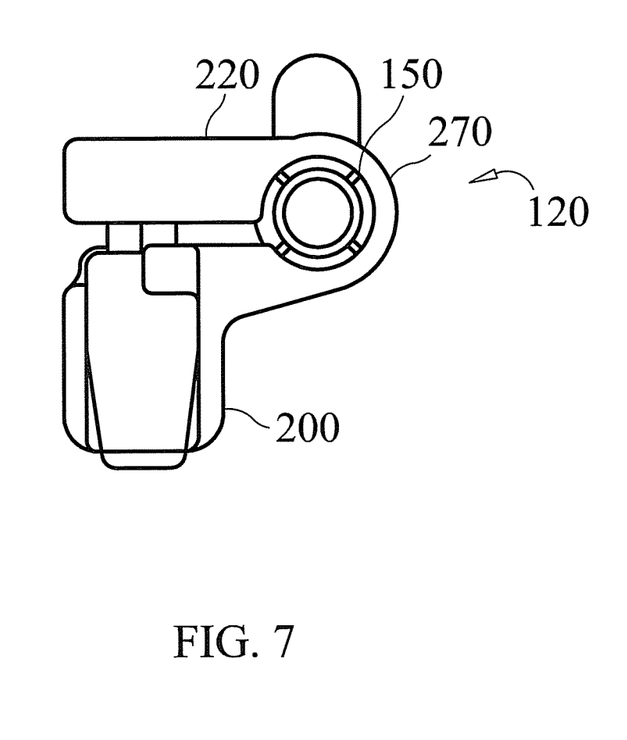
FIG. 7 illustrates the side view of the transverse connector system and specifically the clamping element according to an embodiment of the invention.

FIG. 7 illustrates a side view of the transverse connector. This view more clearly illustrates the clamping element in one particular embodiment of the present invention. As shown, the clamping element 220 is integrally formed with the base element 220 and extends to form a C clamp 270. Within the C-clamp of the clamping element 220, there is provided a collet 150. When a fastener is advanced within the screw hole of the clamping element, the pressure is applied to the spherical collet thereby capturing the transverse rod which is positioned within the C clamp. When the fastener is not advanced the transverse rod is able to move in any angle and can be moved laterally since there is no pressure applied to the clamping element.

Figures 8, 9:
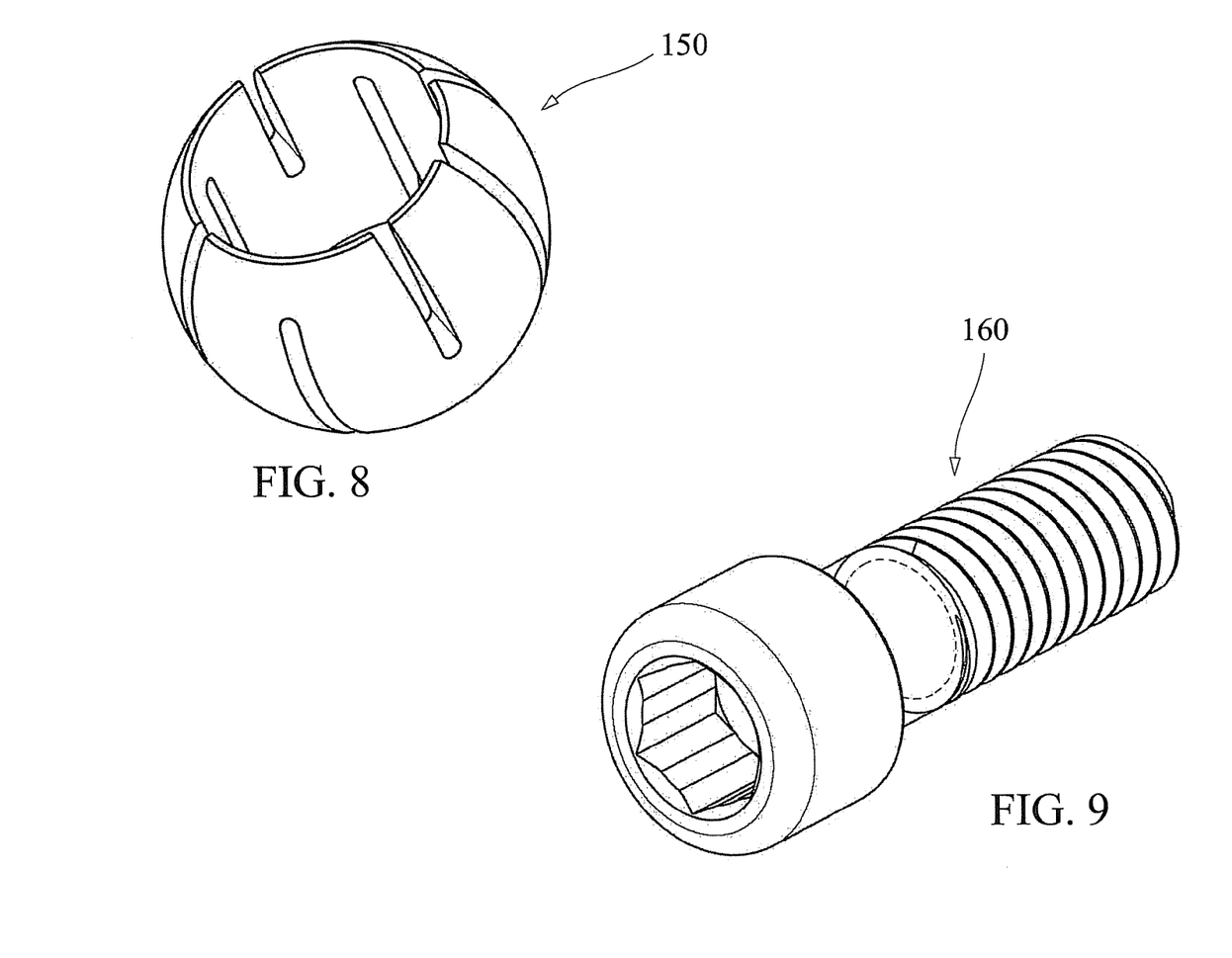
FIG. 8 is a perspective view of a spherical collet according to one aspect of the invention.
FIG. 9 illustrates a fastener according to one aspect of the invention.

FIG. 8 illustrates the spherical collet that is positioned within the C-claim. The spherical collet 150 forms a collar around the transverse rod and exerts a strong clamping force on the object when it is tightened. When pressure is not applied upon the spherical collet, the transverse rod is able to rotate in any angle and can be translated in laterally. It should be noted that collets can range in holding capacity from zero to several inches in diameter. The most common type of collet is one that grips a round bar or tool, but there are collets for square, hexagonal, and other shapes.

Figures 10, 11:
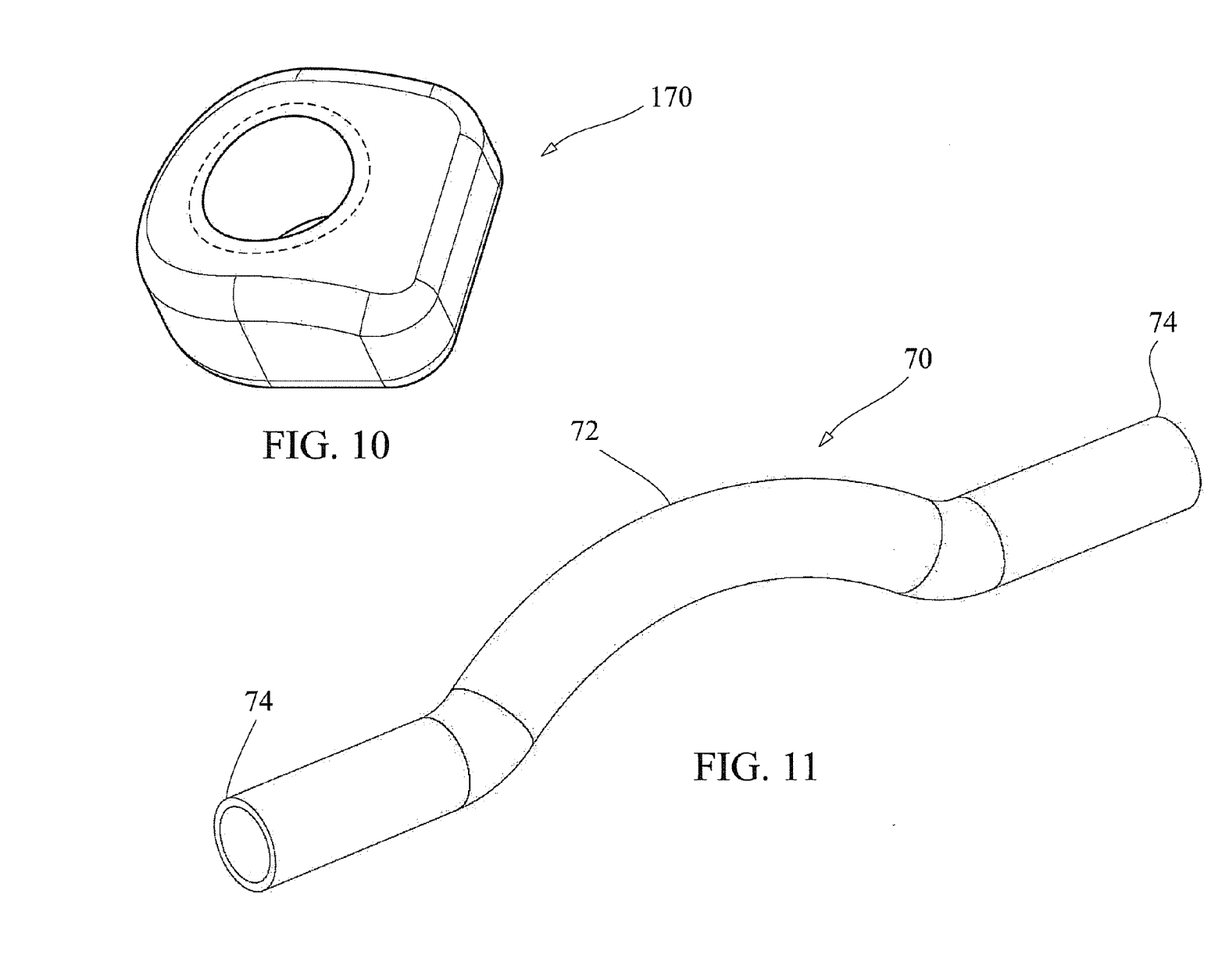
FIG. 10 illustrates a nut according to one aspect of the invention.
FIG. 11 illustrates a transverse rod according to one aspect of the invention.

FIGS. 9 and 10 illustrate a screw and a nut that may be used in one particular embodiment of the present invention. The screw is a fastening means that is used to fasten the clamping element and is configured to be received by a nut 170. The screw is generally threaded and is adapted to be received by the screw hole on the top portion of the base element 120. The nut 170 is generally positioned to receive the screw within the base element 120. Any type of screw that facilitates the fastening of the clamping element and the pivot arm may be used in the invention The screw in one particular embodiment can be provided with threads along its elongate shaft. In order to aid in tightening the screw, the screw may include projections with a curved surface to aid in gripping the screw. The length of the elongate shaft be varied depending on the size and configuration of the locking head.

FIG. 11 illustrates the transverse rod 70, which is attached to the locking heads. Although the rod 70 illustrated is provided with a curved middle portion 72, the transverse rod 70 can be designed with or without a curved portion. The ends 74 of the rod 70 are designed so that they can be moved laterally within the clamping element of the locking head. However, the traverse rod 70 in one embodiment cannot be removed from the clamping section of the locking heads. The transverse rod 70 can be designed and manufactured so that each edge 74 is slightly larger than the collet. As a result, the transverse rod 70 cannot be removed from the clamping element of the locking heads.

Figure 12:
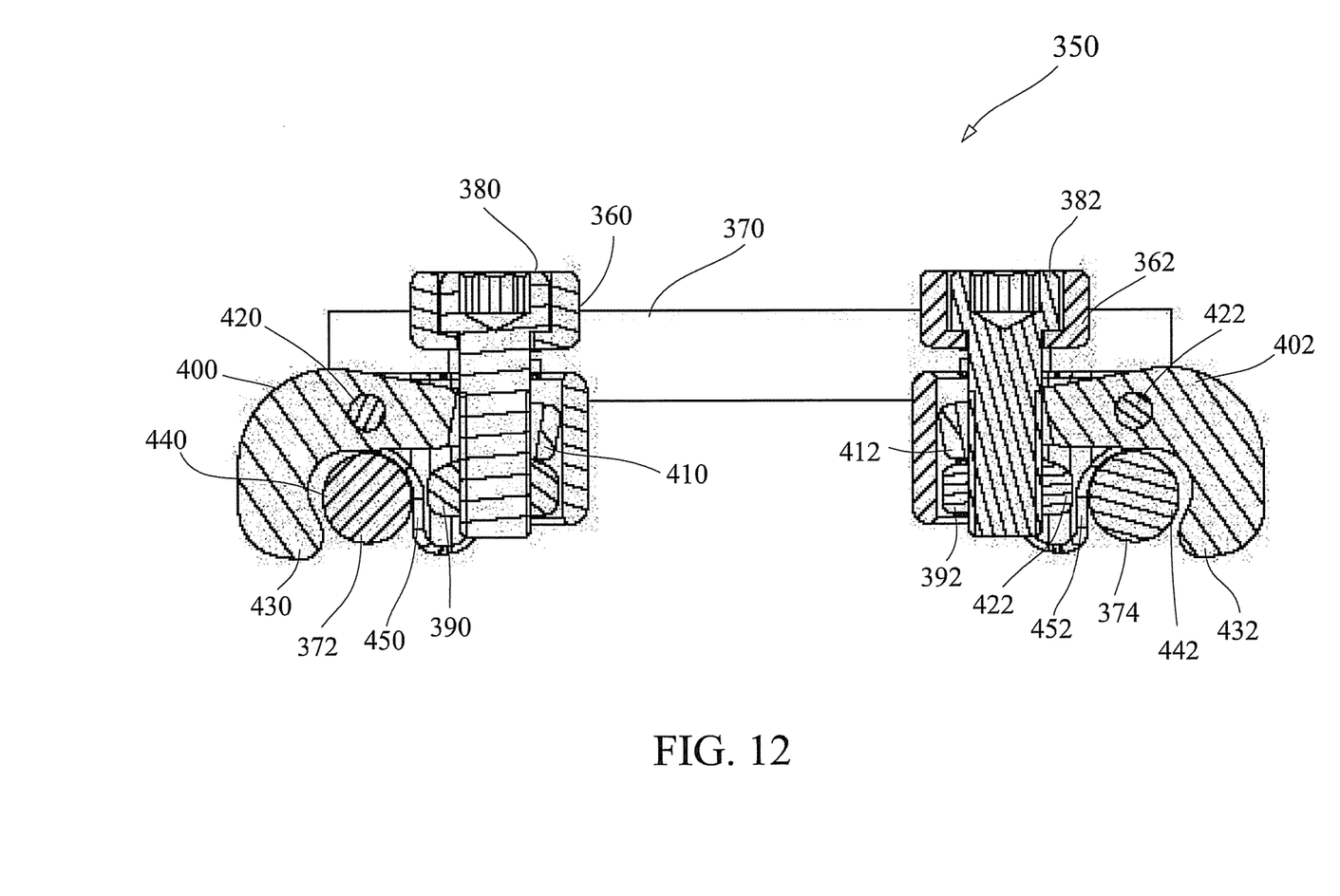
FIGS. 12 and 13 illustrate cross-sectional views of the transverse connector in an open and closed position.
Figure 13:
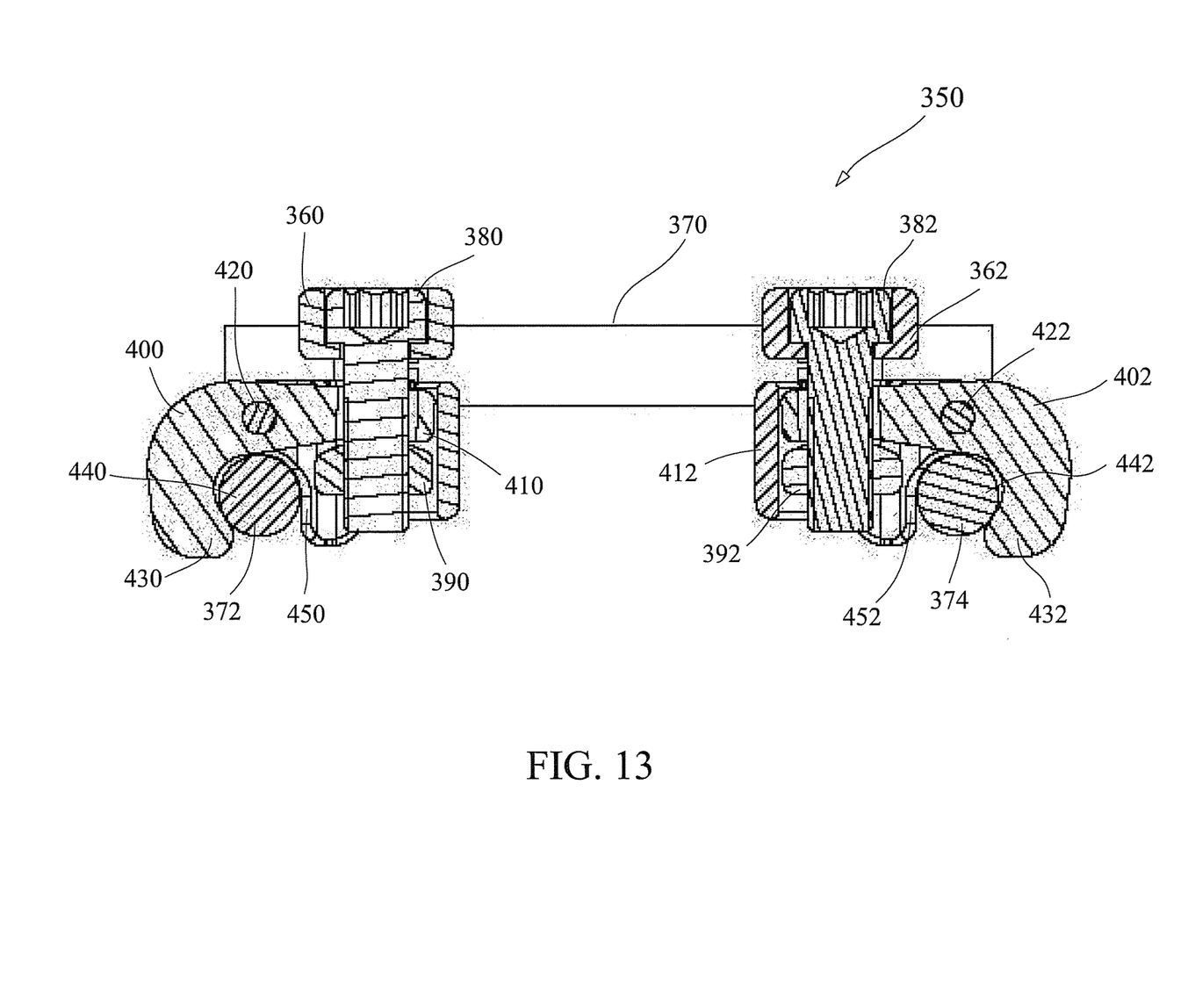

FIGS. 7, 12 and 13 will be used to describe the simultaneous capturing and retaining mechanism according to the present invention. FIG. 12 shows the open position of the pivot arm whereas FIG. 13 shows the pivot arm in a closed position. Since each locking head operates substantially the same, the locking mechanism of a single locking head will be described.

The cross-sectional view of the transverse connector 350 as shown in FIGS. 12 and 13 clearly illustrate the elements utilized by the locking heads 360 and 362 to secure the transverse rod 370 and elongated rods 372 and 374. The screws 380 and 382 are positioned within the screw hole of the locking heads 360 and 362 and through the serrated nuts 390 and 392. As the screw is turned and advanced into the screw hole, the clamping element is tightened (FIG. 7) thereby retaining and capturing the transverse rod in one specific angle and position. Simultaneously, as the screw 380 is advanced through the use of a screw driver, the nut 390 is advanced vertically and applies pressure upon the pivot arm 400. Specifically, the nuts 390 and 392 contact the bottom portion of the pivot arm 410, and 412 which causes the pivot arm 401, 402 to pivot at the pivot point 420 and 422. As the pivot arm 400, 402 pivots, the hooking element 430 and 432 applies pressure upon a first portion 440, 442 of the elongated rod against the base element 450, 452, as shown in FIG. 13. As a result, the elongated rods 372, 374 are captured and retained in a tight lock between the hooking element 430, 432 of the pivot arm 400 and the curved edge 450, 452 of the base element. It should be noted that the present invention is not limited to a screw as a fastening means. Any type of fastening device which applied pressure upon the clamping element and simultaneously applied pressure upon the bottom portion arm would be compatible with the present invention.

It should be further noted that each locking head is fastened separate from the other. For instance, the first locking head 360 is fastened to secure the first portion of the transverse rod and the first elongated rod. Then the second locking head 362 is fastened to secure the second portion of the transverse rod and the second elongated rod.

There are several major benefits of the invention for use in the human spine. First of all is the single step locking mechanism. This allows the surgeon to lock the construct with a single fastener, reducing surgery times. Second is the large amount of flexibility that is afforded to the surgeon in angular as well as linear adjustment. Because of the poly-axial connection between the gripping heads and the connecting rod, either end can be translated along the rod to account for rod spacing and can be adjusted to any angle necessary. Third is the top loading nature of the design. This allows for easy insertion and locking.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A transverse connector system for coupling first and second elongated rods comprising:
   a first and a second locking head;
   a transverse rod having opposing first and a second ends, the first end being retained within a portion of the first locking head and the second end being retained within a portion of the second locking head; and
   a first pivot pin and a second pivot pin;
   wherein the first locking head has a first pivot arm for engaging and capturing the first elongated rod and the second locking head has a second pivot arm for engaging and capturing the second elongated rod, wherein the first pivot arm rotates around the first pivot pin and the second pivot arm rotates around the second pivot pin;
   wherein the first locking head simultaneously secures the first end of the transverse rod and the first elongated rod and the second locking head simultaneously securing the second end of the transverse rod and the second elongated rod
   wherein the first and second locking heads comprise a first and second screw hole,
   wherein a first and second fastener are inserted into the first and second screw holes, wherein when the first and second fastener are advanced in the first and second screw holes, the first and second clamping elements secure and retain the transverse rod and the pivot arm secures and retains the elongated rod simultaneously.

2. The transverse connector system as provided in claim 1, wherein the first and second elongated rods are parallel to one another.

3. The transverse connector system according to claim 1, wherein the first locking head further comprises a clamping element.

4. The transverse connector system according to claim 3, wherein the clamping element comprises a collet.

5. The transverse connector system according to claim 1, wherein transverse rod is securable in any angle by the first and second locking heads.

6. The transverse connector system according to claim 1, wherein the first locking head includes at least two lateral elements extending from a first base element of the first locking head and the second locking head includes at least two lateral elements extending from a second base element of the second locking head.

7. The transverse connector system according to claim 1, wherein the transverse rod is curved.

\* \* \* \* \*